United States Patent [19]

Brown et al.

[11] 4,307,091

[45] Dec. 22, 1981

[54] PROCESS FOR TREATMENT OF ALLERGIC CONDITIONS WITH BENZOXAZINEDIONES

[75] Inventors: Richard E. Brown, East Hanover, N.J.; Vasil St. Georgiev, New Rochelle, N.Y.; Bernard Loev, Scarsdale, N.Y.; Robert Mack, Valley Stream, N.Y.

[73] Assignee: USV Pharmaceutical Corporation, Tuckahoe, N.Y.

[21] Appl. No.: 149,078

[22] Filed: May 12, 1980 (Under 37 CFR 1.47)

[51] Int. Cl.$^3$ ............................................. A61U 27/00
[52] U.S. Cl. ............................ 424/248.4; 424/248.5; 424/248.55; 424/248.57; 424/248.58

[58] Field of Search ............. 424/248.4, 248.5, 248.55, 424/248.57, 248.58

[56] References Cited

PUBLICATIONS

Chem. Abst., 60-10693c (1964).
Weindinger et al., *Chem. Ber.* 97-1599 (1964).
Dickorè et al., *Lieb. Ann. Chem.*, 733 70 (1970).
Grippenberg et al., *Acta Chem. Scand.*, 19-1051 (1965).

*Primary Examiner*—Stanley J. Friedman

[57] ABSTRACT

Therapeutic compositions containing as active principle, a benzoxazindione or pharmaceutically-acceptable acid addition salt thereof are useful in the treatment of allergy.

9 Claims, No Drawings

PROCESS FOR TREATMENT OF ALLERGIC CONDITIONS WITH BENZOXAZINEDIONES

This invention relates to a pharmaceutical composition containing as active principle a benzoxazindione or pharmaceutically-acceptable acid addition salt thereof which is useful in the treatment of asthma and other allergic reactions. The term benzoxazindione as used herein will be understood to include the sulfur-containing analogs except where expressly stated otherwise.

A number of benzoxazindiones and their preparation have been reported in the literature (viz., K. Dickore et al., *Lieb. Ann. Chem.* 733, 70 (1970); J. Grippenberg et al. *Acta Chem. Scand.* 19, 1051 (1965); German Pat. No. 1,161,080 (1964); E. Puxeddo et al., *Gazz. Chem. Ital.* 61, 15158 (1931) and 62, 558 (1932); and, H. Weindinger et al., *Chem. Ber.* 97 1599 (1964), each of which is incorporated by reference herein).

It has now been surprisingly found that certain known benzoxazindiones and still others described for the first time herein have been found to possess potent anti-allergic activity. Thus, in accordance with the present invention, a pharmaceutical composition is provided comprising as active principle thereof an anti-allergic compound of the general formula:

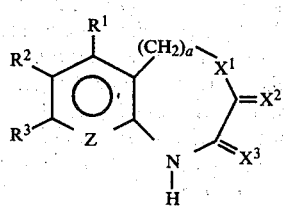

wherein, $R^1$, $R^2$ and $R^3$ is hydrogen, alkyl, alkenyl, alkynyl, aryl, aralkyl, aralkenyl, hydroxy, alkoxy, alkenyloxy, alkynyloxy, aryloxy, aralkyloxy, halogen, cyano, nitro, carboxy formyl, carbalkoxy, carbaryloxy, hydroxyalkyl, amino, alkylamino, trihalomethyl, mercapto, trihalomethoxy, alkylthio, aminoalkyl; methanesulfonyl, or $R_1$ and $R_2$ or $R_2$ and $R_3$ when taken together form methylenedioxy;

Z is N or $CR^1$;
a is 0 or 1; and
$X^1$, $X^2$, and $X^3$ each is O or S, and pharmaceutically-acceptable acid addition salts thereof, together with a pharmaceutical excipient therefore.

The 1,4-benzoxazindiones, which up to the present are preferred, are represented by the general formula:

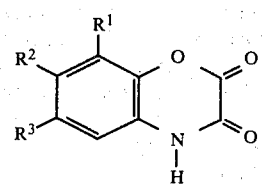

wherein $R^1$, $R^2$, and $R^3$ each is hydrogen, alkyl, alkenyl, aryl, aralkyl, alkaryl, alkoxy, halo or nitro.

Various methods for the preparation of the benzoxazindiones herein are known. Thus, for example, ortho-amino phenols and ortho-amino benzyl alcohols can be reacted with oxalyl dichloride according to the equation

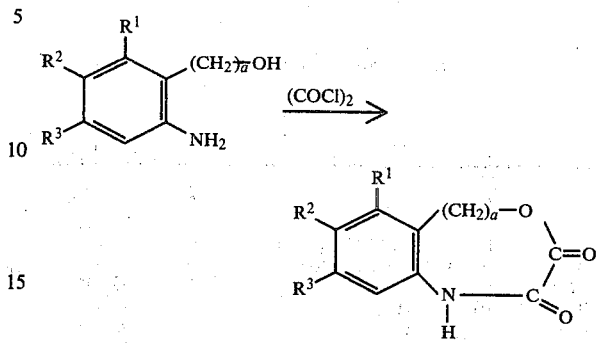

wherein $R^1$, $R^2$ and $R^3$ and a each have the same meanings given above.

The following examples are illustrative of the preparation of anti-allergic compounds in accordance with this invention:

EXAMPLE 1

4H-1,4-Benzoxazin-2,3-dione.

Ortho-aminophenol (21.8 g) in 200 ml of ortho-dichlorobenzene was added as a slurry to 18.3 ml oxalyl dichloride (1.05 mol eq) in 150 ml ortho-dichlorobenzene at about 100° C. with stirring. After the addition (about 30 min.), the reaction mixture was heated to about 70° C. and then kept at this temperature for approximately 1.5 hours. The reaction mixture was then cooled, filtered and the solid product, 4H-1,4-benzoxazin-2,3-dione was washed with ether to give 27 g., m.p. 265°–268° C.

EXAMPLE 2

4H-1,4-Benzoxazin-2-one-3-thione

A mixture of 25 g of 4H-1,4-benzoxazin-2,3-dione and 14.3 ml of thionylchloride in 500 ml of toluene and 5 ml dimethylformamide was heated at about 130° C. until all solids dissolved (about 2–3 hours). The solution was decanted hot (if the solution was deeply colored, charcoal was added and following stirring, the solution was filtered) and the organic solution was evaporated to dryness to give 29 g of 3-chloro-4H-1,4-benzoxazin-2-one, m.p. 133°–136° C.

A solution of 3.6 g of sodium sulfide hydrate in 15 ml of water saturated with hydrogen sulfide was added dropwise to a solution of 5.45 g of 3-chloro-4H-1,4-benzoxazin-2-one in 30 ml of tetrahydrofuran at −150° C. The mixture was stirred one hour to 0° C. The tetrahydrofuran was evaporated and the precipitated filtered and recrystallized from toluene to provide the solid product 4H-1,4-benzoxazin-2-one-3-thione, m.p. 215°–220° C.

Employing methods similar to those illustrated above the following benzoxazindiones were prepared:

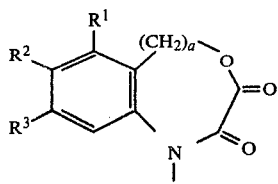

| R¹ | R² | R³ | a | m.p. (°C.) |
|---|---|---|---|---|
| H | CH₃ | H | 0 | — |
| H | H | CL | 0 | 306–309 |
| H | CN | H | 0 | 298–302 |
| H | H | NHCOCO₂C₂H₅ | 0 | 266–268 |
| H | —CH=CH—CH=CH— | | 0 | 300 |
| NO₂ | H | H | 0 | 268–274 |
| H | OH | H | 0 | 184–186 |
| H | CF₃ | H | 0 | 208–213 |
| H | OCH₃ | H | 0 | 248–252 |
| H | COOH | H | 0 | >300 |
| OCH₃ | H | H | 0 | 247–249 |
| H | OCH₃ | OCH₃ | 0 | 269–272 |
| H | H | OCH₃ | 0 | 249–253 |
| OCH₃ | H | CH₂=CH—CH₂— | 0 | 204–206 |
| | | COOCH₃ | 0 | 232–234 |
| OCH₃ | | COOCH₃ | 0 | 285–287 |
| H | H | —(CH₂)₄— | 0 | 262–266 |
| H | H | H | 1 | 186–189 |
| H | —CH=CH—CH=CH— | | 0 | >300 |

Using the same procedures as previously described or employing methods described in the literature the following compounds, including compounds described in the literature, can be prepared:

[Structure with R¹, R², R³, Z, (CH₂)ₐ, X¹, X², X³, N-R⁴]

| Z | R¹ | R² | R³ | X¹ | X² | X³ |
|---|---|---|---|---|---|---|
| CH | H | H | H | O | O | O |
| CH | H | CH₃ | H | O | O | O |
| CH | H | H | H | O | O | O |
| CH | H | H | Cl | O | O | O |
| CH | H | CN | H | O | O | O |
| CH | H | H | NO₂ | O | O | O |
| CH | H | OH | H | O | O | O |
| CH | H | H | CF₃ | O | O | O |
| CH | H | OCH₃ | H | O | O | O |
| CH | H | COOH | H | O | O | O |
| CH | OCH₃ | H | H | O | O | O |
| CH | H | OCH₃ | OCH₃ | O | O | O |
| CH | H | CH₃ | CH₃ | O | O | O |
| CH | H | H | CH₂C₆H₅ | O | O | O |
| CH | H | H | C(CH₃)₃ | O | O | O |
| CH | H | H | C₆H₅ | O | O | O |
| CCOOH | H | H | H | O | O | O |
| CCl | Cl | Cl | Cl | O | O | O |
| CCl | Cl | H | Cl | O | O | O |
| CH | Cl | H | Cl | O | O | O |
| CH | OCH₃ | H | CH₂=CH—CH₂ | O | O | O |
| N | H | H | H | O | O | O |
| N | H | CH₃ | H | O | O | O |
| CH | H | H | H | S | O | O |
| CH | H | H | H | O | S | O |
| CH | H | CH₃ | H | O | O | S |
| CH | H | CH₃ | CH₃ | O | S | S |
| CH | H | H | H | S | S | S |
| CH | H | H | H | O | O | S |

The benzoxazindiones as described herein are therapeutically useful as such or can be employed in the form of salts with a wide variety of acids, inorganic and organic, including therapeutically-acceptable acids. The salts with therapeutically-acceptable acids are, of course, useful in the preparation of formulations where water solubility is desired.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, glyconic, gulonic, succinic, arylsulfonic, e.g., p-toluenesulfonic acids, and the like. The pharmaceutically-unacceptable acid addition salts, while not useful for therapy, are valuable for isolation and purification of the substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the anti-allergenic compounds herein.

The present new compounds can form conjugates with amino acids and the sugar acids. For example, conjugates can be formed with glucuronic acid, e.g., β-D-glucuronic acid, as well as amino acids especially alpha amino acids, such as glycine, lysine, cystine, methionine, aspartic acid, alanine and the like. The conjugates with pharmaceutically-acceptable amino acids and glucuronic acid are especially useful in formulation of therapeutic dosage forms.

As therapeutic agents, the present benzoxazindiones are particularly useful as anti-allergic agents, acting via inhibition of mediator release. The benzoxazindiones are active orally in the Rat Passive Cutaneous Anaphylaxis (PCA) Screen as described by I. Mota, *Life Sciences*, 7, 465 (1965) and Z. Ovary, et al., *Proceedings of Society of Experimental Biology and Medicine*, 81, 584 (1952); and inhibit histamine release from passively sensitized rat mast cells according to the procedure described by E. Kusner, et al., *Journal of Pharmacology and Experimental Therapeutics*.

The therapeutic agents of this invention may be administered alone or in combination with pharmaceutically-acceptable carriers, the proportion of which is determined by the solubility and chemical nature of the compound, chosen route of administered and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples illustrate the preparation of suitable dosage forms for the anti-allergic compounds of the invention. For convenience, the anti-allergic compounds are represented as "active compound" in the description. Of course, each of the formulations can be employed with the anti-allergic compounds described hereinbefore.

FORMULATION 1

| Ingredients | Quantity per 10,000 Tablets |
| --- | --- |
| 1. Active Compound | 60 g. |
| 2. Lactose, USP | 600 g. |
| 3. Microcrystalline Cellulose, NF | 134 g. |
| 4. Directly compressible Starch | 200 g. |
| 5. Magnesium Stearate, USP | 6 g. |
| | 1000 g. |

Method of Preparation
A. Blend 1, 2, 3, and 4. Pass through a #30 mesh screen.
B. Add 5 and blend.
C. Compress into 9/32 inch tablets using a suitable tablet press to obtain about 10,000 mg. tablets.

FORMULATION 2

| Ingredients | Quantity per 10,000 Tablets |
| --- | --- |
| 1. Active Compound | 120 g. |
| 2. Lactose, USP | 870 g. |
| 3. Microcrystalline Cellulose, NF | 200 g. |
| 4. Directly compressible Starch | 300 g. |
| 5. Magnesium Stearate, USP | 10 g. |
| | 1500 g. |

Method of Preparation
A. Blend 1, 2, 3, and 4. Pass through #30 mesh screen.
B. Add 5 and blend.
C. Compress into 5/16 inch tablets using a suitable tablet press to obtain about 10,000 12 mg. tablets.

FORMULATION 3

| Ingredients | Quantity per 10,000 Capsules |
| --- | --- |
| 1. Active Compound | 6 g. |
| 2. Lactose, USP | 193 g. |
| 3. Magnesium Stearate, USP | 1 g. |
| | 200 g. |

Method of Preparation
A. Blend 1 with a small portion of 2. Pass through a #40 mesh screen.
B. Blend Step A mixture with the remainder of 2.
C. Add 3 and blend.
D. Encapsulate the blend in 1000 #4 two-piece hard gelatin capsules which contain 6 mg. each.

FORMULATION 4

| Ingredients | Quantity per 1000 Capsules |
| --- | --- |
| 1. Active Compound | 12.0 g. |
| 2. Lactose, USP | 286.5 g. |
| 3. Magnesium Stearate, USP | 1.5 g. |
| | 300.0 g. |

Method of Preparation
A. Blend 1 with a small portion of 2. Pass through a #40 mesh screen.
B. Blend step A mixture with the remainder of 2.
C. Add 3 and blend.
D. Encapsulate the blend in 1000 #3 two-piece hard gelatin capsules which contain 12 mg. each.

FORMULATION 5

| Ingredients | Quantity per 1000 ml. |
| --- | --- |
| 1. Active Compound | 1.2 g. |
| 2. Sodium Benzoate, USP | 1.0 g. |
| 3. Saccharin Sodium, NF | 0.5 g. |
| 4. Glycerin | 50.0 ml. |
| 5. Sorbitol Solution 70%, USP | 100.0 ml. |
| 6. Sugar, granulated | 500.0 g. |
| 7. FD&C Yellow No. 6 | 0.1 g. |
| 8. Imitation Orange Flavor | 5.0 ml. |
| 9. Water, Purified USP qs to | 1000.0 ml. |

This composition contains 6.0 mg. of active compound per 5 ml. of syrup.
Method of Preparation.
A. Dissolve 1 in about 300 ml. of 9 with agitation.
B. Continue agitation and dissolve 2, 3, and 6 in the batch.
C. Add 4 and 5 and mix until the batch is homogeneous.
D. In a separate container dissolve 7 in about 10 ml. of 9, and add this solution into the batch mix.
E. Add 8 and bring the batch to volume with 9.
F. Mix until the batch is homogeneous.
G. Filter through a suitable filter press.

FORMULATION 6

| Ingredients | Quantity per 1000 ml. |
| --- | --- |
| 1. Active Compound | 2.4 g. |
| 2. Sorbitol Solution 70%, USP | 80.0 g. |
| 3. Glycerin, USP | 20.0 g. |
| 4. Methylparaben, USP | 1.5 g. |
| 5. Propylparaben, USP | 0.5 g. |
| 6. Sodium Citrate (dihydrate), USP | 5.0 g. |
| 7. Sugar, granulated | 150.0 g. |
| 8. FD&C Red No. 4 | 0.1 g. |
| 9. Imitation Cherry Flavor | 4.0 mg. |
| 10. Water, Purified USP qs to | 1000.0 ml. |

This composition contains 12.0 mg. of active compound per 5 ml. of syrup.
Method of Preparation
A. Dissolve 1 in about 500 ml. of 10 with agitation.
B. Continue agitation and dissolve 6 and 7.
C. Add 2 and 3 and mix until the batch is homogeneous.
D. In a separate container, dissolve 4 and 5 in about 100 ml. of hot (80°) 10. Add to the batch.
E. Prepare separately a solution of 8 in about 10 ml. of 10 and add to the batch. Mix.
F. Add 9 to the batch and bring to volume with 10. Mix until homogeneous.
G. Filter through a suitable filter press.

FORMULATION 7

| Ingredients | Weight Percent |
| --- | --- |
| 1. Active Compound | 2.0 |
| 2. Alcohol, USP | 34.0 |
| 3. Propellant 12 | 64.0 |
| | 100.0 |

Method of Preparation
A. Dissolve 1 in 2 and cool to about 0°.
B. Add chilled 3 in Step A solution.
C. Fill the appropriate quantity in a metered aerosol container.

| FORMULATION 8 | |
|---|---|
| Ingredients | Weight, Percent |
| 1. Active Compound | 1.0 |
| 2. Alcohol, USP | 19.0 |
| 3. Propellant 12 | 30.0 |
| 4. Propellant 114 | 50.0 |
| | 100.0 |

Method of Preparation.
A. Dissolve 1 in 2.
B. Fill the appropriate quantity of Step A solution along with a mixture of 3 and 4 in a metered aerosol container.

What is claimed is:

1. A method of treating allergy which comprises administering to a host in need of such treatment an anti-allergic effective amount of a compound of the structure

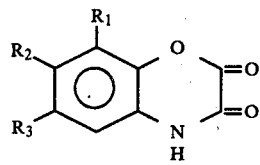

wherein
  $R_1$, $R_2$ and $R_3$ are independently selected from the group consisting of hydrogen, alkyl, alkenyl, hydroxy, alkoxy, carboxy, carbalkoxy, halogen, trifluoromethyl, cyano, nitro, and amino.

2. A method according to claim 1 wherein
  $R_1$ is hydrogen,
  $R_2$ is methoxy, and
  $R_3$ is methoxy.

3. A method according to claim 1 wherein
  $R_1$ is hydrogen,
  $R_2$ is methyl, and
  $R_3$ is hydrogen.

4. A method according to claim 1 wherein
  $R_1$ is hydrogen,
  $R_2$ is cyano, and
  $R_3$ is hydrogen.

5. A method according to claim 1 wherein
  $R_1$ is hydrogen,
  $R_2$ is hydroxy, and
  $R_3$ is hydrogen.

6. A method according to claim 1 wherein
  $R_1$ is hydrogen,
  $R_2$ is hydrogen, and
  $R_3$ is chloro.

7. A method according to claim 1 wherein
  $R_1$ is hydrogen,
  $R_2$ is hydrogen, and
  $R_3$ is nitro.

8. A method according to claim 1 wherein
  $R_1$ is methoxy,
  $R_2$ is hydrogen, and
  $R_3$ is hydrogen.

9. A method according to claim 1 wherein
  $R_1$ is hydrogen,
  $R_2$ is carboxy, and
  $R_3$ is hydrogen.

* * * * *